United States Patent [19]

Belagaje et al.

[11] Patent Number: 4,738,921
[45] Date of Patent: Apr. 19, 1988

[54] DERIVATIVE OF THE TRYPTOPHAN OPERON FOR EXPRESSION OF FUSED GENE PRODUCTS

[75] Inventors: Ramamoorthy Belagaje; Janet K. Epp; JoAnn Hoskins; Hansen M. Hsiung; George L. Long, all of Indianapolis; Brigitte E. Schoner, Zionsville, all of Ind.

[73] Assignee: Eli Lilly and Company, Indianapolis, Ind.

[21] Appl. No.: 655,183

[22] Filed: Sep. 27, 1984

[51] Int. Cl.$^4$ .................. C12P 21/00; C12P 21/02; C12N 15/00; C12N 1/20; C12N 7/00; C07H 15/12

[52] U.S. Cl. .................. 435/68; 435/70; 435/172.3; 435/253; 435/320; 435/849; 536/27; 935/41; 935/47; 935/48

[58] Field of Search .............. 435/68, 70, 172.3, 317, 435/253; 935/39, 40, 41, 73; 536/27

[56] References Cited

FOREIGN PATENT DOCUMENTS 0036776 9/1981 European Pat. Off. .
0128733 1/1984 European Pat. Off. .
0123228 10/1984 European Pat. Off. .
0130166 1/1985 European Pat. Off. .
0155655 9/1985 European Pat. Off. .

OTHER PUBLICATIONS

Darlix et al., *Nucleic Acids Research*, 10(17):5183–5196, 1982
Peters et al., 1984, J. Cell, Biochem., 8(A):295.
Mullenbach et al., 1983, Fed. Proc., 42(7):1832.
Miozzari and Yanovsky, 1978, Journal of Bacteriology, 133(3):1457.
Rinderknecht and Humbel, 1976, Proc. Natl. Acad. Sci. U.S.A., 73(12):4379.
Rindernecht and Humbel, 1978, Journal of Biological Chemistry, 253(8):2769.
Klapper et al., 1983, Endocrinology, 112(6):2215.
Rinderknecht and Humbel, 1978, Febs Letters, 89(2):283.
Blundell and Humbel, 1980, Nature, 287:781.
Spencer et al., 1983, Proceedings of a Symposium on Insulin-Like Growth Factors/Somatomedins, pp. 81–96.
Ullrich et al., 1984, EMBO Journal, 3(2):361.
Jansen et al., 1983, Nature, 306:609.
Bell et al., 1984, Nature, 310:775.
Li et al., 1983, Proc. Natl. Acad. Sci. U.S.A., 80:2216.
Patent Classification Definitions Class 935, U.S. Patent and Trademark Office, Feb., 1984, pp. 935–16 and 935–17.
Schoner et al., 1984, Proc. Natl. Acad. Sci., U.S.A., 81:5403–5407.
George et al., 1985, DNA, 4(4):273–281.
Peden, 1983, Gene, 22:277–280.
P. Stanssens et al., Gene, 36 211 (1985).
W. L. Sung et al., PNAS, 83, 561 (1986).
Itakura; K. et al., Science, 198, 1056 (1977).
M. G. Shepard et al., DNA, 1, 125 (1982).
H. A. de Boer et al., DNA, 2, 231 (1983).
P. H. Seeburg et al., DNA, 2, 37 (1983).

*Primary Examiner*—Thomas G. Wiseman
*Assistant Examiner*—Thomas D. Mays
*Attorney, Agent, or Firm*—Ron K. Levy; Leroy Whitaker

[57] ABSTRACT

The present invention comprises improved derivatives of the tryptophan operon useful for expressing fused gene products in *E. coli* and relate organism. Two of the improved derivatives disclosed are encoded on 0.43 and 0.55 kb EcoRI restriction fragments from plasmids pCZ20 and pLEBGH2 (in strains NRRL B-15881 and NRRL B-15882), respectively. The modified derivatives have been placed on recombinant DNA cloning and expression vectors. A variety of expression vectors have been constructed that drive expression of fused gene products. Two novel gene sequences, encoding insulin-like growth factors I and II, have been expressed with the modified tryptophan operon system.

49 Claims, 8 Drawing Sheets

Restriction Site and Function Map of Plasmid pCZ20
(10.7kb)

Restriction Site and Function Map of
Plasmid pCZ20
(10.7kb)

Restriction Site and Function Map of
Plasmid pLEBGH2
(6.0kb)

Restriction Site and Function Map of
Plasmid pIGF201
(4.6kb)

Restriction Site and Function Map of
Plasmid pIGF202
(4.8kb)

Restriction Site and Function Map of
Plasmid pIALE1
(4.8kb)

Restriction Site and Function Map of
Plasmid pIBLE2
(5.0kb)

Restriction Site and Function Map of
Plasmid pPILE1
(5.1kb)

DERIVATIVE OF THE TRYPTOPHAN OPERON FOR EXPRESSION OF FUSED GENE PRODUCTS

SUMMARY OF THE INVENTION

The present invention is an improved, shortened derivative of the tryptophan operon. The tryptophan (trp) operon of *Escherichia coli* has been used to investigate virtually every aspect of amino acid metabolism, operon structure and gene structure and function. Miozzari et al., 1978, J. Bacteriol. 133: 1457-1446 constructed a plasmid containing the trp promoter-operator and portions of the leader sequence and trpE gene. A deletion removing the sequence encoding the carboxy terminal portion of the leader peptide, the entire attenuator region of the leader sequence and the sequence encoding the amino terminal portion of trpE led to the production of a fused gene product, LE. The derivative of the trp operon produced by this deletion is useful in the production of fused gene products comprising the LE peptide and a polypeptide of research or commercial value.

The present invention comprises improved derivatives of the modified trp operon constructed by Miozzari. These improved derivatives were made by introducing deletions in the LE-encoding region. Two well-characterized deletions, trpLE1 and trpLE2, are especially useful. Expression vectors containing either trpLE1 or trpLE2 were constructed to drive expression of fused gene products in *Escherichia coli*. When fused to small proteins such as insulin-like growth factors I and II, these altered LE proteins represent a much smaller fraction of the fused gene product than would be the case if the original LE protein was present. This is extremely advantageous as it provides for a greater recovery of the desired protein.

The invention further comprises a novel DNA sequence encoding the gene for insulin-like growth factor II and a novel on a sequence encoding the gene for insulin-like growth factor I. Additionally, the invention comprises expression vectors and transformants comprising the aforementioned DNA sequences.

The present invention is related generally to European Patent Application No. 0036776, filed on Sept. 30, 1981. The aforementioned application discloses plasmids employing a modified tryptophan operon that has been useful as an expression system (Miozzari et al., 1978). This deletion allows maximal derepression of the tryptophan operon and high expression of polypeptide products. The publication does not, however, disclose the present modified tryptophan operons or suggest their utility as critical components of improved expression vectors and methods.

The present invention also provides for the cloning and expression of synthetic insulin-like growth factors I and II (IGFI and IGFII) gene sequences in *Escherichia coli* and related organisms. Somatomedins, such as IGFI and IGFII, constitute a heterogeneous group of peptides with important growth-promoting effects in vitro as well as in vivo. Such peptides are believed to mediate the growth-promoting actions of growth hormone and may be useful in the treatment of: dwarfism, osteoporosis, cartilage degeneration, heart and skeletal muscle deterioration, wounds and protein and carbohydrate dysfunction. Heretofore, IGFs could be isolated from human plasma in which they are present in extremely small quantities. Research in the area of IGF function has been extremely limited because of the general paucity of available, purified IGF. The present invention overcomes this limitation since the cloning and expression of these synthetic genes by way of recombinant DNA technology provides an efficient means of producing large quantities of these important proteins and thus represents a significant advance in the technical art.

For purposes of the present invention, as disclosed and claimed herein, the following terms are as defined below.

Recombinant DNA Cloning Vector—any autonomously replicating or integrating agent, including, but not limited to, plasmids, comprising a DNA molecule to which one or more additional DNA segments can be or have been added.

Recombinant DNA Expression Vector—any recombinant DNA cloning vector into which one or more transcriptional and translational activator sequence(s) has been incorporated.

Transcriptional Activating Sequence—any DNA sequence that directs or provides for the transcription of DNA into a mRNA transcript.

Translational Activating Sequence—any DNA sequence that provides for the translation of a mRNA transcript into a polypeptide.

Leader Sequence—a segment of an operon between the transcriptional activating sequence and the structural gene(s); in the trp operon, a portion of the leader sequence encodes a leader peptide.

TrpLE—a DNA segment encoding that portion of the tryptophan operon consisting of the promoter, the operator, the sequence encoding the amino terminal portion of the leader peptide and the sequence encoding the carboxy terminal portion of trpE; thus, trpLE drives expression of a fused gene product called LE.

Functional Polypeptide—a recoverable bioactive heterologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bioinactivating polypeptide which can be specifically cleaved.

Restriction Fragment—any linear DNA sequence generated by the action of one or more restriction enzymes.

Fused Gene Product—a recoverable heterologous polypeptide which is fused with a portion or whole of a homologous polypeptide.

Replicon—any DNA sequence that controls the replication of recombinant DNA cloning and expression vectors.

Runaway Replicon—a replicon which lacks or can be induced to lose copy number control, such loss resulting in the uncontrolled replication and an extreme increase in the copy number of DNA into which such replicon has been incorporated.

Transformation—the introduction of DNA into a recipient host cell that changes the genotype and results in a change in the recipient cell.

Transformant—a recipient host cell that has undergone transformation.

$Ap^R$—the ampicillin-resistant phenotype.

$Km^R$—the kanamycin-resistant phenotype.

EK-BGH—the enterokinase-bovine growth hormone sequence.

DETAILED DESCRIPTION OF THE INVENTION

The present invention is an improved derivative of the tryptophan operon comprising a transcriptional activating sequence, a translational activating sequence and a fused leader-trpE gene sequence from which the sequence encoding the carboxy terminus of the leader peptide, the attenuator region and proximal region of the trpE gene have been deleted, wherein the improvement comprises a shortened LE-encoding sequence, said shortened LE-encoding sequence contained within a trpLE sequence comprising about 428 to about 548 deoxyribonucleotide pairs. The invention further comprises expression vectors and transformants comprising the aforementioned DNA.

As discussed above, the present invention can be used to drive expression of various functional polypeptides in *Escherichia coli*. A number of researchers have reported the use of the tryptophan operon regulatory region to express foreign genes in *E. coli*. The majority of expression vectors containing the tryptophan operon which are in use at the present time contain the trp leader sequence (Edman et al., 1981, Nature 291: 503; Miozzari et al., 1978, J. Bacteriology 133: 1457, Kleid et al., European Patent Application EP0036 770 A2; and Goeddel et al., 1980, Nature 287: 411). The vectors are quite useful in expression systems but, given their extensive leader sequences, are limited in their ability to efficiently produce desired proteins due to the large percentage of leader polypeptide in the fused gene product.

The trpLE1 and trpLE2 sequences of the present invention are, respectively, about 428 and about 548 base pairs. The nucleotide sequence of the trpLE1 coding strand is:

that the translational reading phase was not altered upon subsequent ligation to a gene encoding a protein of interest.

By deleting internal regions of the LE sequence, the EcoRI restriction sites which bound the present trpLE1 and trpLE2 sequences were left intact for use in subsequent ligations. The aforedescribed trpLE1 and trpLE2 sequences can be conveniently modified to facilitate ligation if the EcoRI sites are not desired. In addition to the present LE1 and LE2 sequences, many other internal deletions which retain the desired reading phase can be constructed resulting in trpLE sequences that are also within the scope of the present invention. These sequences can be modified by adding, eliminating, or substituting nucleotides to alter characteristics and to provide a variety of unique or additional restriction sites. Those skilled in the art understand nucleotide chemistry and the genetic code and thus which nucleotides are interchangeable and which DNA modifications are desirable for a specific purpose.

The deletions described herein result in significantly truncated LE polypeptide products, thereby diminishing the overall energy and amino acid precursor requirements of the host and enhancing cellular economy and efficiency. Furthermore, the difference in the molecular weight of LE1 and LE2 proteins allows one the option to produce fused gene products of differing size. This is very beneficial when the expression of small polypeptides is desired. As is known in the art, small polypeptides are extremely difficult to obtain using direct expression methods; therefore, expression systems utilizing a fusion protein are often preferred to enhance recovery of the desired protein. The availability of both the LE1 and LE2 sequences, in conjunction with their adaptability, provides an opportunity to

| GA  | ATT | CAC | GCT | GTG | GTG | TTA | TGG | TCG | GTG | GTC | GCT | AGG |
|-----|-----|-----|-----|-----|-----|-----|-----|-----|-----|-----|-----|-----|
| GTG | CCG | ACG | CGC | ATC | TCG | ACT | GCA | CGG | TGC | ACC | AAT | GCT |
| TCT | GGC | GTC | AGG | CAG | CCA | ATC | GGA | AGC | TGT | GGT | ATG | GCT |
| GTG | CAG | GTC | GTA | TAA | TCA | CCG | CAT | AAT | TCG | AGT | CGC | TCA |
| AGG | CGC | ACT | CCC | GTT | CCG | GAT | AAT | GTT | TTT | TGC | TCC | GAC |
| ATC | ATA | ACG | GTT | CCG | GCA | AAT | ATT | CTG | AAA | TGA | GCT | GTT |
| GAC | AAT | TAA | TCA | TCG | AAC | TAG | TTA | ACT | AGT | ACG | CAA | GTT |
| CAC | GTA | AAA | AGG | GTA | TCG | ACA | ATG | AAA | GCA | ATT | TTC | GTA |
| CTG | AAA | GGT | TCA | CTG | GAC | AGA | GAT | CAT | TCT | GTT | CCG | CAG |
| TCG | GAA | GCC | GAC | GAA | ACC | CGT | AAC | AAA | GCC | CGC | GCT | GTA |
| CTG | CGC | GCT | ATT | GCC | ACC | GCG | CAT | CAT | GCA | CAG | GAA | TTC | and the respective coding strand for trpLE2 is:

achieve greater expression results. In the case of very

| GA  | ATT | CAC | GCT | GTG | GTG | TTA | TGG | TCG | GTG | GTC | GCT | AGG |
|-----|-----|-----|-----|-----|-----|-----|-----|-----|-----|-----|-----|-----|
| GTG | CCG | ACG | CGC | ATC | TCG | ACT | GCA | CGG | TGC | ACC | AAT | GCT |
| TCT | GGC | GTC | AGG | CAG | CCA | ATC | GGA | AGC | TGT | GGT | ATG | GCT |
| GTG | CAG | GTC | GTA | TAA | TCA | CCG | CAT | AAT | TCG | AGT | CGC | TCA |
| AGG | CGC | ACT | CCC | GTT | CCG | GAT | AAT | GTT | TTT | TGC | TCC | GAC |
| ATC | ATA | ACG | GTT | CCG | GCA | AAT | ATT | CTG | AAA | TGA | GCT | GTT |
| GAC | AAT | TAA | TCA | TCG | AAC | TAG | TTA | ACT | AGT | ACG | CAA | GTT |
| CAC | GTA | AAA | AGG | GTA | TCG | ACA | ATG | AAA | GCA | ATT | TTC | GTA |
| CTG | AAA | GGT | TCA | CTG | GAC | GGC | AGC | TAC | GGC | GGC | GCG | GTA |
| GGT | TAT | TTC | ACC | GCG | CAT | GGC | GAT | CTC | GAC | ACC | TGC | ATT |
| GTG | ATC | CGC | TCG | GCG | CTG | GTG | GAA | AAC | GGT | ATC | GCC | ACC |
| GTG | CAA | GCG | GGT | GCT | GGT | GTA | GTC | CTT | GAT | TCT | GTT | CCG |
| CAG | TCG | GAA | GCC | GAC | GAA | ACC | CGT | AAC | AAA | GCC | CGC | GCT |
| GTA | CTG | CGC | GCT | ATT | GCC | ACC | GCG | CAT | CAT | GCA | CAG | GAA |
| TTC |     |     |     |     |     |     |     |     |     |     |     |     | wherein A is deoxyadenyl, G is deoxyguanyl, C is deoxycytidyl and T is thymidyl.

The above sequences were constructed by internally deleting various regions within the LE-encoding sequence of trpLE. These deletions were performed such small peptides, a somewhat intermediately sized LE-encoding sequence, such as that in trpLE2, is preferred over the extremely shortened LE-encoding sequence in trpLE1. For example, the expression of the B chain of insulin, a very small polypeptide of 30 amino acids, was greater when fused with trpLE2 than with trpLE1. Also, in certain cases the ultimate purification of desired protein products is facilitated by reduction of the fused gene product's size and complexity.

Another attribute of the present trpLE sequences lies in the resultant changes in the chemical composition and amino acid sequence of the fused gene product. For example, the absence of any cysteine codons in the trpLE1 sequence insures that no internal disulfide bonds will be produced within the LE1 peptide. Additionally, the presence of only one methionine codon in trpLE1 and two methionine codons in trpLE2, confers great purification advantages, as fewer protein fragments are generated upon cyanogen bromide cleavage of the fused gene product and fewer proteins need to be separated than when using unimproved trpLE. In contrast, the known trpLE sequence has seven methionine codons and thus purification after cyanogen bromide cleavage of the fused gene product is difficult and time-consuming.

Expression vectors were constructed containing either the trpLE1 or trpLE2 nucleotide sequences. The sequences were individually fused to genes encoding small proteins, such as bovine growth hormone, proinsulin, the A and B chains of insulin and IGFI and IGFII, for expression in *E. coli*. Thus, the invention further comprises recombinant DNA expression vectors for the production in *Escherichia coli* and related hosts of a heterologous polypeptide product, said vector comprising:

(a) a tryptophan operon promoter-operator and shortened leader-encoding sequence;
(b) a nucleotide sequence encoding a structural gene for a heterologous polypeptide, said nucleotide sequence located downstream and in translational reading phase with the tryptophan promoter-operator and shortened leader-encoding sequence; and
(c) a replicon and selectable marker that provide for vector replication and allow selection in a microorganism transformed by the vector.

The present vectors are extremely advantageous when used to express desired proteins. The fusion of the present trpLE1 or trpLE2 sequence to a gene encoding a protein of interest allows one to produce a larger percentage of the desired protein. This result is evident whenever a finite amount of product can be accumulated per bacterial cell. It follows that a decreased amount of undesirable product, that is, the LE protein, results in an increased amount of the desired protein. Thus, the present vectors, utilizing the trpLE1 and trpLE2 sequences of the present invention, are extremely advantageous, especially as applied to the production of commercially desirable proteins.

Expression vector pCZ20 is approximately 11 kb and contains genetic sequences encoding trpLE1, a synthetic gene for IGFI and a runaway replicon. Plasmid pLEBGH2 is approximately 6 kb and contains genetic sequences encoding trpLE2 and enterokinase-linked bovine growth hormone (EK-BGH). Plasmids pCZ20 and pLEBGH2 can be isolated from *E. coli* K12 RV308/pCZ20 and *E. coli* K12 RR1/pLEBGH2 respectively. The strains have been deposited and made part of the stock culture collection of the Northern Regional Research Laboratory, Peoria, Ill. 61604 and are available to the public as a source and stock reservoir of the plasmids under the respective accession numbers NRRL B-15881 and B-15882. Detailed restriction site and function maps of plasmids pCZ20 and pLEBGH2 are respectively presented in FIGS. 1 and 2 of the accompanying drawings. Figure legends appear from the text. For purposes of the present application, FIG. 1 and all subsequent figures are not necessarily drawn to scale.

For convenience and ease of construction, an ~0.43 kb EcoRI trpLE1-containing restriction fragment can be isolated from plasmid pCZ20 and used as a starting material to construct numerous derivative plasmids. For example, the construction of plasmid pLEBGH1 is performed by first digesting plasmid pLEBGH2 with EcoRI restriction enzyme and then separating the ~5.5 kb EcoRI fragment (containing the gene encoding the EK-BGH polypeptide and an *E. coli* replicon) from the ~0.55 kb EcoRI restriction fragment containing the trpLE2 sequence. Subsequently, the ~0.43 kb EcoRI restriction fragment containing the trpLE1 sequence is ligated to the ~5.5 EcoRI restriction fragment to form plasmid pLEBGH1. Additionally, trpLE1 and trpLE2 can independently be ligated to an EcoRI restriction fragment containing an *E. coli* replicon, a functional antibiotic resistance gene and a synthetic IGFII-encoding gene to form plasmids pIGF201 and pIGF202, respectively.

Plasmids pIGF201 and pIGF202 were constructed to express the IGFII polypeptide under the control of trpLE1 and trpLE2, respectively. Since the nucleotide sequence of the gene encoding IGFII had not, prior to this invention, been isolated or determined, a synthetic gene was constructed. The synthesis of the coding region of the IGFII gene was completed given the knowledge that IGFII consists of 67 amino acids in the following sequence:

| Ala | Tyr | Arg | Pro | Ser | Glu | Thr | Leu | Cys | Gly | Gly | Glu | Leu |
|-----|-----|-----|-----|-----|-----|-----|-----|-----|-----|-----|-----|-----|
| Val | Asp | Thr | Leu | Gln | Phe | Val | Cys | Gly | Asp | Arg | Gly | Phe |
| Tyr | Phe | Ser | Arg | Pro | Ala | Ser | Arg | Val | Ser | Arg | Arg | Ser |
| Arg | Gly | Ile | Val | Glu | Glu | Cys | Cys | Phe | Arg | Ser | Cys | Asp |
| Leu | Ala | Leu | Leu | Glu | Thr | Tyr | Cys | Ala | Thr | Pro | Ala | Lys |
| Ser | Glu | | | | | | | | | | | |

(see, for example, Blundell et al., 1980, Nature 287: 781–787).

From the above amino acid sequence, a corresponding synthetic gene sequence has been invented, subject to a number of specific non-obvious criteria, and oligonucleotide fragments synthesized which, when assembled, form a synthetic gene coding for IGFII. The fragments have been hybridized and ligated in predetermined stages to construct the IGFII gene in two portions. These two portions have been cloned into plasmid pBR322 so as to produce a full length IGFII gene flanked only by plasmid pBR322 DNA. The trpLE1- and trpLE2-containing fragments were inserted into the IGFII-containing pBR322 vector to maximize expression of the gene in *E. coli* and related organisms. A fused gene product comprising IGFII has been expressed in *E. coli*.

Given the above amino acid sequence and the degenerative nature of the genetic code, it is possible to predict numerous nucleotide sequences which would code for IGFI and IGFII. In the inventive determination of an optimum sequence from the large number of sequences possible, several non-obvious criteria have been applied. Firstly, the trinucleotide codons used in the sequence were those known to be accepted or preferred by *E. coli*. Secondly, different restriction enzyme recognition sites were placed at the termini of the molecule so as to allow insertion into a plasmid in a desired orientation. Moreover, it was decided to select sites which allowed the use of well-understood cloning vectors, such as plasmid pBR322. In fact, EcoRI and BamHI recognition sites were selected and introduced at the 5' and 3' ends, respectively, of the IGFI- and IGFII-encoding sequence. Thirdly, a series of restriction endonuclease recognition sites were strategically placed along the molecule to enable the gene to be specifically dissected to aid characterization and, possibly, mutagenesis. In particular, a PstI site was introduced at a central location in the IGFII gene. The placement of restriction enzyme recognition sites allowed the two portions of the molecule to be cloned in stages. Fourthly, since the protein ultimately expressed in bacterial cells was to be in the form of a fusion product, it was desirable to have a means of cleaving the IGFII portion from such a fusion product. The codon specifying the amino acid methionine was introduced near the end of the gene corresponding to the IGFII amino-terminus in order for there to be a methionine present in the fusion product to serve as a substrate for cyanogen bromide cleavage. Fifthly, two stop codons were introduced at the end of each gene to prevent read-through translation.

The particular preferred sequence selected for the coding region of the synthetic IGFII gene is as follows:

| | | | |
|---|---|---|---|
| GCTTATCGAC | CGTCTGAAAC | TCTGTGCGGC | GGCGAACTGG |
| TTGACACTCT | GCAGTTCGTT | TGCGGCGACC | GTGGCTTCTA |
| CTTCTCTCGT | CCGGCTTCTC | GTGTTTCTAG | ACGTTCTCGT |
| GGCATCGTTG | AAGAATGCTG | CTTCCGCTCT | TGCGACCTGG |
| CTCTGCTGGA | AACTTACTGC | GCTACTCCTG | CTAAATCTGA A | wherein A is deoxyadenyl, G is deoxyguanyl, C is deoxycytidyl and T is thymidyl.

Plasmid pCZ20 contains the synthetic IGFI gene of the present invention. The preferred DNA sequence encoding IGFI, contained within plasmid pCZ20 is as follows:

| | | | |
|---|---|---|---|
| 5'-GGCCCGGAAA | CTCTGTGCGG | CGCTGAACTG | GTTGACGCTC |
| TGCAGTTCGT | TTGCGGCGAC | CGTGGCTTCT | ACTTCAACAA |
| ACCGACTGGC | TACGGCTCTT | CTTCTCGTCG | TGCTCCGCAG |
| ACTGGCATCG | TCGACGAATG | CTGCTTCCGT | TCTTGCGACC |
| TGCGTCGTCT | GGAAATGTAC | TGCGCTCCGC | TGAAACCTGC |
| TAAATCTGCT-3' | | | | wherein A is deoxyadenyl, G is deoxyguanyl, C is deoxycytidyl and T is thymidyl. The IGF-1 encoding gene sequence, including the amino acids tryptophan and methionine, can be isolated on an ~230 bp EcoRI-BamHI restriction fragment of plasmid pCZ20.

The present vectors for expressing functional polypeptides in *E. coli* represent a significant technical advance. The aforedescribed trpLE1 and trpLE2 DNA sequences can be used for the universal expression in *E. coli* and related organisms of any polypeptide-encoding gene. While specific embodiments of the invention are shown and described in the following examples, many variations are possible. For example, the present invention is in no way limited to the use of a particular polypeptide-encoding gene since the choice of a specific sequence is not critical to the operability of the present invention. Genes coding for a functional polypeptide can be substituted for the EK-BGH-, IGFI-, IGFII-, insulin A chain-, insulin B chain- and proinsulin-encoding genes presently exemplified. Such coding sequences include, but are not limited to, sequences that code for human growth hormone, human pregrowth hormone, porcine growth hormone, mammmalian growth hormone, avian growth hormone, growth hormone releasing factor, human pre-proinsulin, human and non-human interferon, viral antigen, urokinase, tissue plasminogen activator, interleukin II, any peptide hormone, any enzyme or virtually any other polypeptide with research or commercial value.

The present vectors are not limited to the use of a specific replicon from a particular *E. coli* plasmid. Although the *E. coli* replicon exemplified in the majority of the present vectors is from plasmid pBR322, other *E. coli* replicon-containing fragments can be obtained from, for example, plasmid pBR324 (disclosed in Bolivar, F., 1978, Gene 4: 121), pBR325 (disclosed in Soberon, X., 1980, Gene 9: 287), plasmid pKN402 (disclosed in Uhlin et al., 1979, Gene, 6: 91–106), or the like to produce novel vectors. Those skilled in the art will understand that ligation of these, or any other, *E. coli* replicon-containing fragments results in vectors that are within the scope of the present invention.

The expression vectors of this invention can be applied to a wide range of host organisms, for example, Gram-negative prokaroytic organisms such as *Escherichia coli*, *E. coli* K12, *E. coli* K12 RV308, *E. coli* K12 HB101, *E. coli* K12 C600R$_k$-M$_k$-, *E. coli* K12 RR1, *E. coli* K12 MM294 and the like. While all of the embodiments of the present invention are useful, some of the vectors and transformants are preferred. Preferred vectors are pCZ20, pLEBGH1, pLEBGH2, pIGF201, pIGF202, pIALE1, pIALE2, pIBLE1, pIBLE2, pPILE1 and pPILE2. Preferred transformants include *E. coli* K12 RV308/pCZ20, *E. coli* K12 RV308/pLEBGH2, *E. coli* K12 RV308/pLEBGH1, *E. coli* K12 RV308/pIGF201, *E. coli* K12 RV308/pIGF202, *E. coli* K12 MM294/pIGF201, *E. coli* K12 MM194/pIGF202, *E. coli* K12 RV308/pIALE1, *E. coli* K12 RV308/pIBLE2, and *E. coli* K12 RV308/pPILE1. Moreover, of this preferred group, plasmids pCZ20, pLEBGH1, pIGF201 and pIBLE2 and transformants *E. coli* K12 RV308/pCZ20, *E. coli* K12 RV308/pLEBGH1, *E. coli* K12 RV308/pIGF201 and *E. coli* K12 RV308/pIBLE2 are especially preferred.

The following examples further illustrate the invention disclosed herein. Both an explanation of and the actual procedures for constructing the invention are described where appropriate.

EXAMPLE 1

Figure 1:
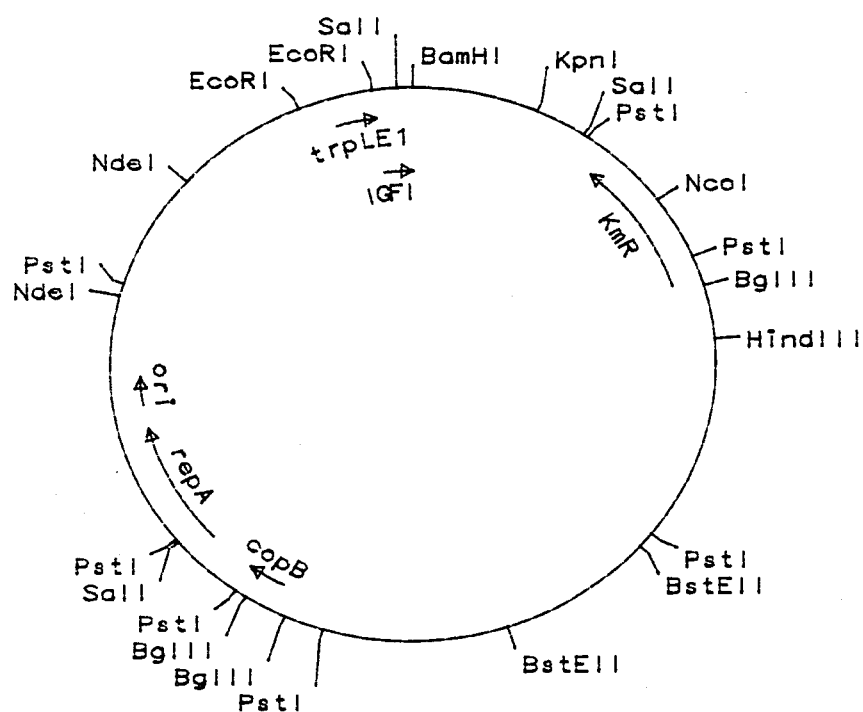
FIG. 1 is a restriction site and function map of plasmid pCZ20.

Culture of *Escherichia coli* RV308/pCZ20 and Isolation of Plasmid pCZ20

A. Culture of *Escherichia coli* RV308/pCZ20

One hundred ml of TY broth (10 g tryptone, 5 g yeast extract and 5 g NaCl per liter) containing 50 µg/ml kanamycin sulfate were inoculated with a culture of *E. coli* RV308/pCZ20 (NRRL B-15881) and incubated with shaking for ~16 hours at 20°-25° C. The 100 ml of culture were then transferred to a flask containing 900 ml TY broth containing with 50 µg/ml kanamycin. The diluted culture was then incubated with shaking of 37° C. for 2-3 hours. The 37° C. temperature of incubation induced high plasmid copy number.

B. Isolation of Plasmid pCZ20

The cells were pelleted by centrifugation (4° C. at 10,000 rpm for 5 minutes) and the pellet resuspended in 20 ml of a solution containing 25 mM Tris-HCl, pH 8; 10 mM EDTA; and 50 mM glucose and supplemented with 2 mg/ml lysozyme. The resuspended cells were incubated on ice for 15 minutes, and then 40 ml of a solution containing 1% SDS and 0.2N NaOH were added and mixed. After the cells were completely lysed, 30 ml of cold 3M NaOAc, pH 4.8, were added, mixed and the resulting solution incubated on ice for one hour. This solution was then centrifuged at 20,000 rpm for 30 minutes. After centrifugation, the pellet was discarded and 3 volumes cold, absolute ethanol were added to the supernatant. The resulting mixture was chilled at −70° C. for 10–20 minutes and then centrifuged at 10,000 rpm for 10 minutes to pellet the DNA.

The DNA pellet was resuspended in 10 ml of TE buffer (10 mM Tris-HCl, pH 7.5 and 1 mM EDTA), and then 0.1 ml of a 5 mg/ml RNAse A solution and 10 µl of a 2500 U/ml RNAse T solution were added. After the RNAses were mixed in with the solution, the solution was incubated at 65° C. for 20 minutes. Next, 30 g of CsCl were added and the volume adjusted to 38 ml, total, with TE buffer. Two ml of ethidium bromide were added, and ultracentrifugation at 49,000 rpm for 17 hours in a vertical rotor was performed to band the plasmid DNA.

After the plasmid band was removed from the centrifugation tube, the ethidium bromide was extracted with isopropanol (saturated with CsCl and H₂O) and the CsCl removed by dialysis against TE buffer. The resultant plasmid pCZ20 DNA was suspended in TE buffer at a concentration of 1 µg/ml and stored at −20° C. A restriction site and function map of plasmid pCZ20 is presented in FIG. 1 of the accompanying drawings.

EXAMPLE 2

Isolation of the ~0.43 kb EcoRI Restriction Fragment Encoding trpLE1 From Plasmid pCZ20

About 30 µl (30 µg) of the plasmid pCZ20 DNA, isolated above, were added to 10 µl 10X EcoRI buffer (1.5M Tris-HCl, pH 7.2; 500 mM NaCl; and 10 mM dithiothreitol), 2 µl EcoRI restriction enzyme (~60 units) and 58 µl H₂O. After mixing, the reaction was placed in a 37° C. water bath for one hour, and then the solution was electrophoresed on a 1% agarose gel until the desired ~0.43 kb EcoRI fragment was clearly separated from the other digestion products. Visualization of the electrophoresed DNA was accomplished by staining the gel in a dilute solution (0.5 µg/ml) of ethidium bromide and exposing the stained gel to long-wave UV light. After locating the desired fragment, a small slit was made in the gel and a small piece of Schleicher and Schuell (Keene, NH 03431) NA-45 DEAE membrane was placed in the slit. Upon further electrophoresis the DNA non-covalently bound to the DEAE membrane. After the desired fragment was bound to the DEAE membrane, the membrane was removed and rinsed with low salt buffer (150 mM NaCl; 0.1 mM EDTA; and 20 mM Tris-HCl, pH 8). Next, the membrane was placed in a small tube and immersed in high salt buffer (1M NaCl; 0.1 mM EDTA; and 20 mM Tris-HCl, pH 8) and then incubated at 65° C. for one hour to remove the DNA from the DEAE paper. After incubation, the incubation buffer was collected and the membrane rinsed with high salt buffer. The rinse solution was pooled with the incubation buffer before collecting the desired DNA fragment.

The volume of the high salt-DNA solution was adjusted so that the NaCl concentration was 0.25M, and then three volumes of cold, absolute ethanol were added. The resulting solution was mixed and placed at −70° C. for 10–20 minutes. After chilling, the solution was centrifuged at 15,000 rpm for 15 minutes. After another precipitation to remove residual salt, the DNA pellet was rinsed with ethanol, dried, resuspended in 20 µl of TE buffer and constituted ~0.25 µg of the desired trpLE1-encoding EcoRI restriction fragment.

EXAMPLE 3

Culture of *Escherichia coli* RV308/pLEBGH2 and Isolation of Plasmid pLEBGH2

A. Culture of *Escherichia coli* RV308/pLEBHG2

One hundred ml of TY supplemented with 50 µg/ml amplicillin and 100 µg/ml tryptophan were inoculated with a culture of *E. coli* RV308/pLEBGH2 (NRRL B-15882) and then incubated at 37° C. for 16 hours with shaking. The culture was then diluted to 1 liter with TY broth containing with 50 µg/ml ampicillin and 100 µg/ml tryptophan and incubation continued until the optical density at 550 nanometers was ~0.5 absorbance units. When this density was reached, one gram of uridine was added to the flask. The uridine was incubated with the cells for 15 minutes, and then 170 mg of chloramphenicol were added. Incubation of the culture at 37° C. with shaking was continued for ~16 hours. The uridine and chloramphenicol additions are a well-known means of amplifying certain E. coli plasmids.

B. Isolation of Plasmid pLEBGH2

Figure 2:
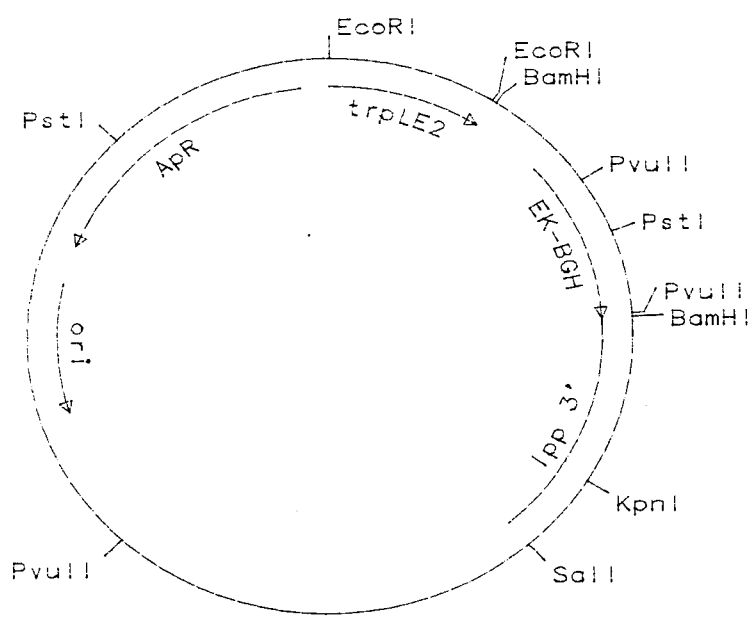
FIG. 2 is a restriction site and function map of plasmide pLEBGH2.
Figure 3:
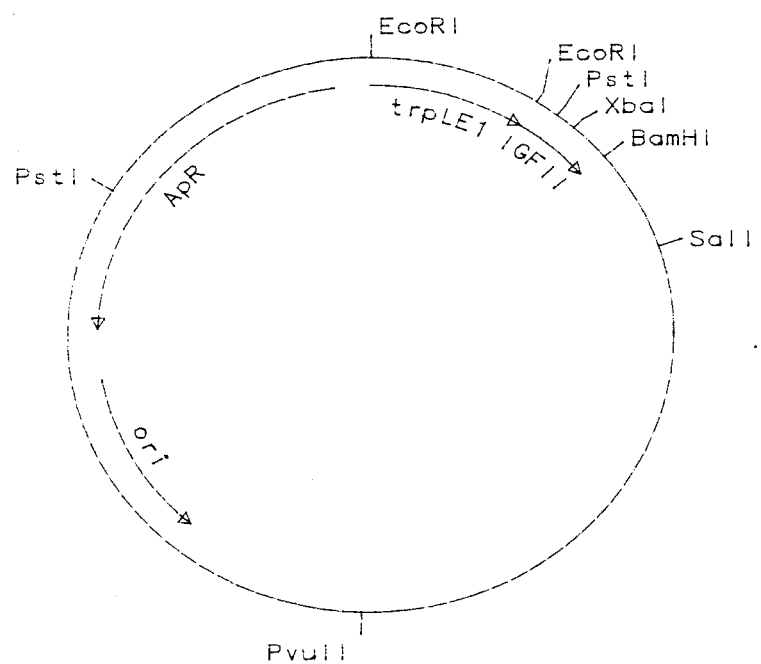
FIG. 3 is a restriction site and function map of plasmid pIGF201.
Figure 4:
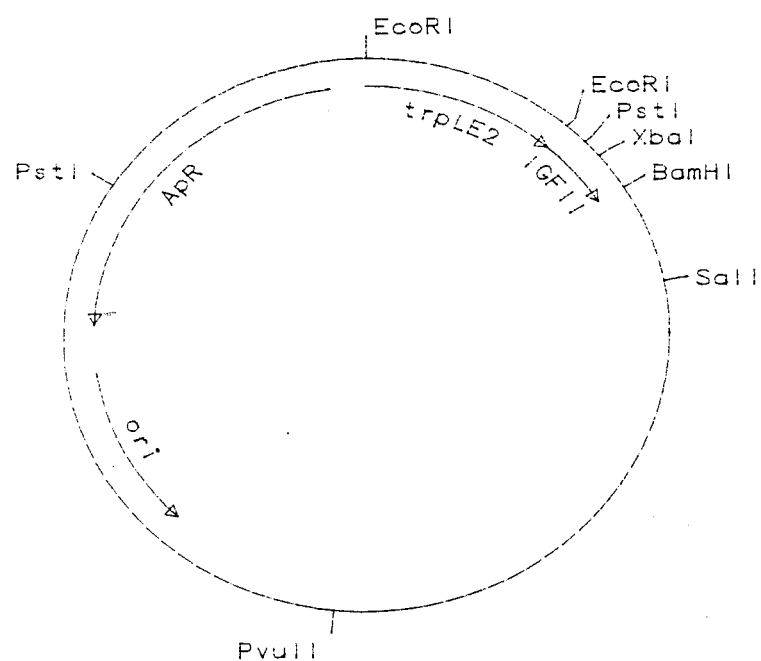
FIG. 4 is a restriction site and function map of plasmid pIGF202.
Figure 5:
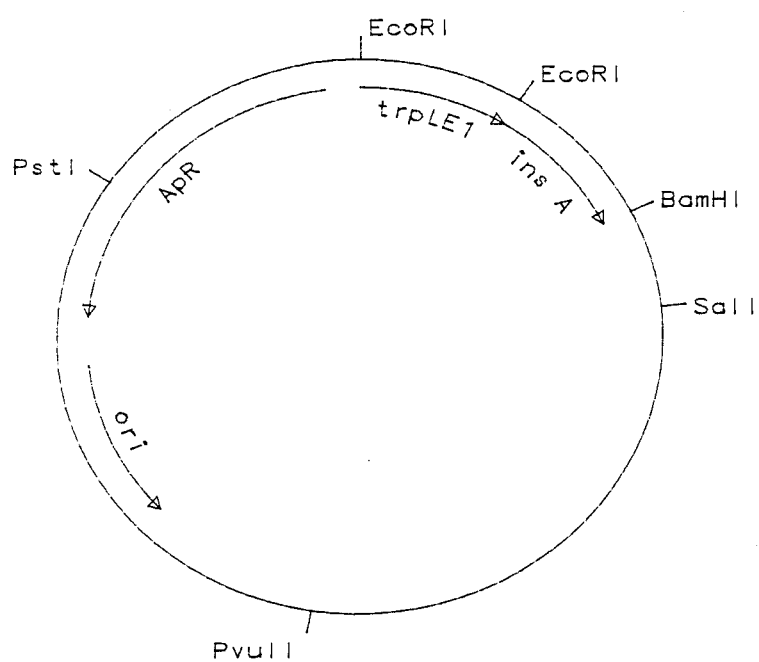
FIG. 5 is a restriction site and function map of plasmid pIALE1.
Figure 6:
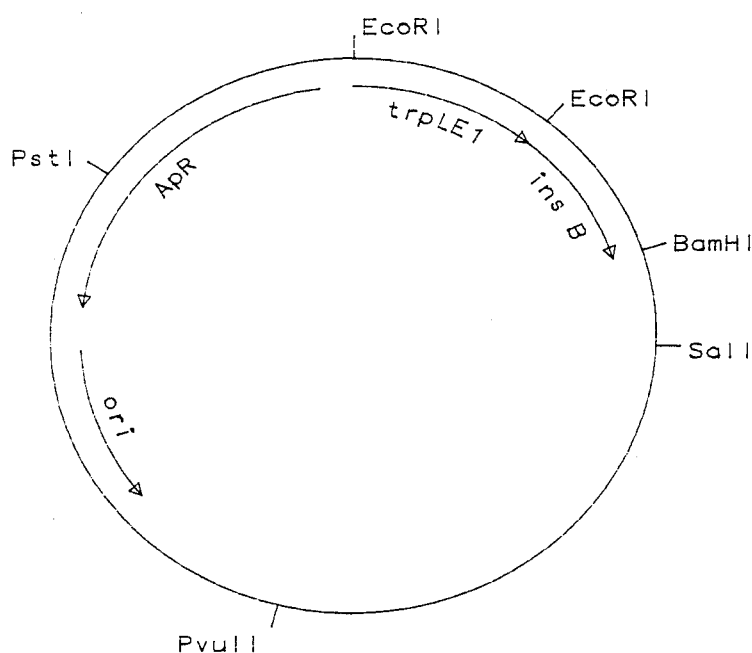
FIG. 6 is a restriction site and function map of plasmid pIBLE2.
Figure 7:
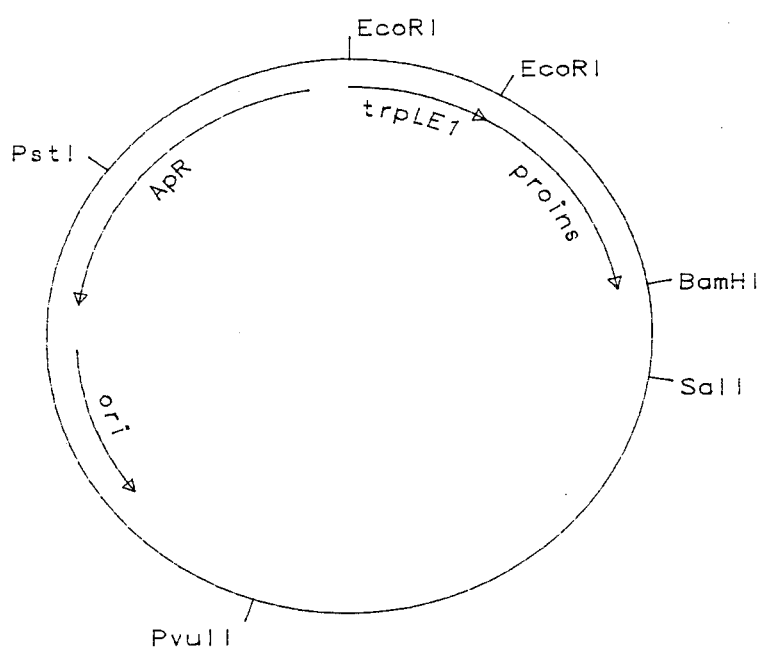
FIG. 7 is a restriction site and function map of plasmid pPILE1.

Plasmid pLEBGH2 was isolated from the above culture in substantial accordance with the procedure of Example 1B. The resultant plasmid, pLEBGH2, was suspended in TE buffer at a concentration of 1 μg/μl and stored at −20° C. A restriction site and function map of plasmid pLEBGH2 is presented in FIG. 2 of the accompanying drawings.

EXAMPLE 4

EcoRI Digestion of Plasmid pLEBGH2

About 30 μl of plasmid pLEBGH2 DNA (from Example 3) were digested with EcoRI and the reaction products isolated in substantial accordance with the procedures of Example 2. Two EcoRI fragments were isolated and purified: (1) the ~0.55 kb EcoRI fragment encoding the trpLE2 sequence; and (2) the ~5.5 kb EcoRI fragment encoding EK-BGH, the pBR322 replicon and the β-lactamase gene. About 0.65 μg of the trpLE2-encoding fragment was obtained and suspended in 20 μl of TE, and about 6.5 μg of the ~5.5 kb fragment were obtained and suspended in 100 μl of phosphatase buffer (10 mM Tris-HCl, pH 8; 1 mM MgCl$_2$; and 0.01 mM ZnCl$_2$).

EXAMPLE 5

Construction of *Escherichia coli* RV308/pLEBGH1

A. Construction of Plasmid pLEBGH1

The ~5.5 kb EcoRI restriction fragment suspended in phosphatase buffer (from Example 4) was incubated at 65° C. for 5 minutes, and then 1 μl (7 units Boehringer-Mannheim) of calf-intestinal alkaline phosphatase was added, mixed and incubation at 65° C. continued for 5 more minutes. The incubation was followed by a 30 minute incubation at 60° C., after which the reaction mix was extracted once with phenol:CHCl$_3$ (50:50) and once with CHCl$_3$. After the extractions, the reaction mix was made 0.3M in NaOAc; two volumes of ethanol were added; and, after mixing and chilling the solution to −70° C., the solution was centrifuged to pellet the phosphatased fragment. The DNA pellet obtained was suspended in 25 μl of TE buffer and constituted ~5 μg of the phosphatased ~5.5 kb EcoRI restriction fragment of plasmid pLEBGH2.

About 1 μl of the phosphatased ~5.5 kb EcoRI fragment was mixed with 4 μl of the purified 0.43 kb EcoRI fragment encoding trpLE1 obtained in Example 2, 2 μl of 5 mM ATP, 2 μl of 10 mM dithiothreitol, 2 μl of 10 X ligase buffer (660 mM Tris-HCl, pH 8 and 60 mM MgCl$_2$), 8 μl of water and 1 μl (800 units New England Biolabs) of T4 DNA ligase. The reaction was incubated at 20° C. for two hours. The ligated DNA was subsequently transformed into E. coli K12 RV308.

B. Construction of *Escherichia coli* RV308/pLEBGH1

1. Preparation of Frozen, Competent *Escherichia coli* K12 RV308 and *Escherichia coli* K12 MM294

Five ml portions of TY broth were individually inoculated with E. coli K12 RV308 (NRRL B-15624) and E. coli K12 MM294 (NRRL B-15625) and the resulting cultures incubated at 37° C. overnight with shaking. The overnight cultures were diluted with TY broth to a final volume of 1 liter, resulting in an optical density reading (600 nanometers) of each culture that was ~0.1 absorbance units. The incubation at 37° C. with shaking was continued until the optical density reading (600 nm) reached the 0.55–0.65 absorbance units range, and then the cells were collected by centrifugation.

The cell pellets were individually resuspended in 500 ml of chilled 50 mM CaCl$_2$ and the resulting mixtures incubated on ice for 15–30 minutes. The cells were then collected by centrifugation, and the resulting pellets were resuspended in 20 ml of a cold solution of 20% glycerol in 50 mM CaCl$_2$. The cell mixtures were then aliquoted in 0.2 ml portions into pre-chilled tubes, which were immediately placed and stored at −70° C. The cells prepared by this procedure remain viable and competent for transformation for up to one year.

2. Transformation

One of the tubes containing the competent E. coli K12 RV308 cells was removed from storage at −70° C., thawed and mixed with the ligated DNA of Example 5A. The cell-DNA mix was incubated on ice for one hour. The cells were then collected, the supernatant discarded and the pellet resuspended in 0.5 ml of TY broth supplemented with tryptophan at 100 μg/ml. After incubation for 30 minutes at 37° C., the cells were plated on TY plates supplemented with 50 μg/ml ampicillin and 100 μg/ml tryptophan. The plates were incubated at 37° C. overnight.

3. Analysis

Since the ligation products prepared in Example 5A comprised both the desired plasmid pLEBGH1 and other undesired plasmids, the individual transformants were analyzed in order to determine in which transformants plasmid pLEBGH1 was present.

Since the entire DNA sequence of plasmid pLEBGH1 could be predicted, the isolated plasmid DNA from the transformed E. coli cells was cleaved with different restriction enzymes to determine, by electrophoresis and gel analysis, whether the reaction products were those predicted for plasmid pLEBGH1. The proteins expressed by the transformants were analyzed in the absence of tryptophan and the desired transformants identified by their production of LE1-EK-BGH (38,000 daltons). LE1-EK-B6H and LE2-EK-BGH also comprise protein encoded by pBR322 DNA. In this manner, E. coli K12 RV308/pLEBGH1 tranformants were identified and isolated.

EXAMPLE 6

Construction of IGFII-Encoding DNA

The synthesis of the coding region of the IGFII gene was accomplished by the following generalized procedure: (A) 38 single-stranded deoxyribooligonucleotides, each containing between 9 and 15 deoxyribonucleotides, were synthesized by the improved phosphotriester method; (B) some of the 38 single-stranded DNA molecules were phosphorylated; and (C) a series of annealing and ligating reactions were done to form two double-stranded DNA molecules, each comprising about half of the coding region of the gene.

The two fragments formed above were ultimately inserted into plasmid pBR322 to construct the entire IGFII coding sequence on a single DNA molecule (see Example 7). A more detailed description of steps A–C is now provided.

A. Synthesis of Single-Stranded DNA Fragments

The 38 deoxyribooligonucleotides listed below in Table 1 were synthesized by the improved phosphotriester method of Hsiung et al., 1983, Nucleic Acids Research, 11: 3227. A variety of DNA-synthesizing instruments are also available, well-known and suitable for synthesizing the single-stranded fragments.

TABLE 1

| # | Sequence | Size |
|---|---|---|
| 1 | AATTCATGGCT | 11 mer |
| 2 | TATCGACCGTCT | 12 mer |
| 3 | GGCGGCGAACTG | 12 mer |
| 4 | AAGCCACGGT | 10 mer |
| 5 | GTTGACACTCTG | 12 mer |
| 6 | CGCCGCAAACGA | 12 mer |
| 7 | GCTTCTACTTC | 11 mer |
| 8 | TCTCGTCCGG | 10 mer |
| 9 | CTTCTCGTGTTT | 12 mer |
| 10 | CTAGACGTTC | 10 mer |
| 11 | TCGTGGCAT | 9 mer |
| 12 | CGTTGAAGAATG | 12 mer |
| 13 | TCTTGCGACCTG | 12 mer |
| 14 | CAGTTCGTTTGC | 12 mer |
| 15 | GCTCTGCTGG | 10 mer |
| 16 | AAACTTACTGC | 11 mer |
| 17 | GCTACTCCTGCT | 12 mer |
| 18 | AAATCTGAATAATAG | 15 mer |
| 19 | CGATAAGCCATG | 12 mer |
| 20 | GTTTCAGACGGT | 12 mer |
| 21 | CAACCAGTTCGC | 12 mer |
| 22 | ACTGCAGAGTGT | 12 mer |
| 23 | CTGCTTCCGC | 10 mer |
| 24 | GGCGACCGTG | 10 mer |
| 25 | GAGAGAAGTAG | 11 mer |
| 26 | GAAGCCGGAC | 10 mer |
| 27 | CTAGAAACACGA | 12 mer |
| 28 | ACGAGAACGT | 10 mer |
| 29 | AACGATGCC | 9 mer |
| 30 | AAGCAGCATTCTTC | 14 mer |
| 31 | TCGCAAGAGCGG | 12 mer |
| 32 | CAGAGCCAGG | 10 mer |
| 33 | AAGTTTCCAG | 10 mer |
| 34 | AGTAGCGCAGT | 11 mer |
| 35 | AGATTTAGCAGG | 12 mer |
| 36 | GATCCTATTATTC | 13 mer |

TABLE 1-continued

| # | Sequence | Size |
|---|---|---|
| 37 | GAAACTCTGTGC | 12 mer |
| 38 | CGCCGCACAGA | 11 mer |

B. Phosphorylation

After purifying each oligonucleotide by thin layer chromatography and reversed phase high pressure liquid chromatography, certain of the 38 single-stranded DNA fragments of Table 1 were phosphorylated according to the teaching of Hsiung et al., 1983, in order to facilitate the ligation and construction of the IGFII gene-encoding DNA fragments. Some of the fragments are depicted as having "$^{32}$P" at their 5' end, since tracer amounts of $[\gamma-^{32}P]$-ATP were used in the phosphorylation reactions.

C. Annealing and Ligation

Fragments 1, 2, 3, 19, 20, 21, 37 and 38 were annealed and ligated to form Duplex I:

Fragments 5, 14, 24, 22, 6 and 4 were annealed and ligated to form Duplex II:

Fragments 7, 8, 9, 25, 26 and 27 were annealed and ligated to form Duplex III:

DNA duplex molecules I, II and III were then mixed and treated with T4 DNA ligase to form a double-stranded molecule with an EcoRI overlap at one end of the molecule and a XbaI overlap at the other end. The ligation product of the reaction involving duplexes I, II and III was purified on a 10% polyacrylamide gel and constitutes about half of the IGFII coding region.

The remainder of the IGFII coding region was synthesized in like manner. Thus, fragments 10, 11, 12, 28, 29 and 30 were annealed and ligated to form Duplex IV:

Fragments 23, 13, 15, 16, 31, 32, 33 and 34 were annealed and ligated to form Duplex V:

Fragments 17, 18, 35 and 36 were annealed and ligated to form Duplex VI:

Duplex DNA molecules IV, V and VI were then ligated together to form the remaining portion of the IGFII coding region. The ligation produced a DNA molecule with an XbaI overlap at one end and a BamHI overlap at the other. The ligation product was purified on a 10% polyacrylamide gel.

EXAMPLE 7

Construction of Plasmids pIGF201 and pIGF202

A. Construction of Plasmid pIGF2

Five μg of plasmid pBR322 are dissolved in 5 μl of TE buffer, and 2 μl 10X BamHI buffer (1.5M NaCl; 60 mM Tris-HCl, pH 7.9; 60 mM $MgCl_2$; and 1 mg/ml BSA), 1 μl BamHI restriction enzyme (~10 Units) and 12 μl $H_2O$ are added, gently mixed and incubated at 37° C. for 2 hours. After the incubation, the BamHI-digested DNA is precipitated and then resuspended in 2 μl 10X EcoRI buffer, 1 μl EcoRI restriction enzyme (~10 Units) and 17 μl $H_2O$. After gentle mixing, the reaction is incubated at 37° C. for 2 hours.

The EcoRI- and BamHI-digested plasmid pBR322 DNA is extracted once with phenol-$CHCl_3$ (50:50), followed by extraction with $CHCl_3$ alone. The DNA is precipitated by making the mixture 0.3M in NaOAc, adding 2.5-3 volumes ethanol, mixing, chilling to -70° C. and centrifuging. The DNA pellet constitutes ~5 μg of the EcoRI- and BamHI-digested plasmid pBR322 DNA. After the DNA is suspended in 25 μl of TE buffer, it is stored at -20° C. for subsequent ligation to the synthetic IGFII-encoding gene fragments prepared in Example 6.

One μl of the EcoRI- and BamHI-digested plasmid pBR322 is added to 0.6 picomoles each of the EcoRI-XbaI and XbaI-BamHI IGFII-encoding fragments generated in Example 6. The DNA molecules are ligated in substantial accordance with the ligation procedure of Example 5. The ligated DNA was used to transform E. coli RV308 in substantial accordance with the transformation procedure taught in Example 5. The desired transformants were identified by their predicted ampicillin-resistant, tetracycline-sensitive phenotype and by analysis of their plasmid DNA. The transformants thus identified constituted the desired E. coli RV308/pIGF2. Plasmid pIGF2 was prepared and purified in substantial accordance with the teaching of Example 3.

B. Digestion and Dephosphorylation of Plasmid pIGF2

Five μl of plasmid pIGF2, isolated above, were digested with EcoRI in a total volume of 50 μl in substantial accordance with the procedure of Example 4. The EcoRI-digested plasmid pIGF2 obtained was pelleted by precipitation, resuspended in 100 μl of phosphatase buffer and then treated with calf-intestinal alkaline phosphates in substantial accordance with the procedure of Example 5A. After removing the phosphatase enzyme, the dephosphorylated EcoRI-digested plasmid pIGF2 was suspended in 25 μl of TE buffer and stored at -20° C.

C. Ligation and Transformation

One μl of the dephosphorylated EcoRI-digested plasmid pIGF2 added to 4 μl of the trpLE1-encoding EcoRI restriction fragment isolated in Example 2 and ligated in substantial accordance with the teaching of Example 5A. The ligated DNA constituted the desired plasmid pIGF201. Plasmid pIGF202 was constructed in like manner, by using 4 μl of the trpLE2-encoding EcoRI restriction fragment prepared in Example 4 in place of the trpLE1-encoding EcoRI fragment.

The ligated DNA constituting plasmids pIGF201 and pIGF202 DNA was individually used to transform both E. coli K12 RV308 and E. coli K12 MM294 in accordance with the transformation procedure of Example 5B2. The desired transformants, E. coli K12 RV308/pIGF201, E. coli K12 MM294/pIGF201, E. coli K12 RV308/pIGF202 and E. coli K12 MM294/pIGF202, were identified by analysis of their plasmid DNA and protein production in the absence of tryptophan.

EXAMPLE 8

Construction of Insulin A Chain, Insulin B Chain, and Proinsulin Expression Vectors A. Isolation of Structural Genes 1. Isolation of the Insulin A Chain Structural Gene The insulin A chain structural gene was obtained from plasmid pIA1; the construction of which is disclosed in Goeddel et al., 1979, Proc. Nat. Acad. Sci. USA, 76: 106. Approximately 50 μg of plasmid pIA1 were digested with BamHI and EcoRI in substantial accordance with the teaching of Example 7A, and the desired ~0.425 kb insulin A chain structural gene-containing EcoRI-BamHI restriction fragment was isolated by polyacrylamide gel electrophoresis and electroelution. Approximately 0.5 μg of the desired fragment was obtained, suspended in 25 μl of TE buffer and stored at -20° C.

2. Isolation of the Insulin B Chain Structural Gene

The insulin B chain structural gene was obtained from plasmid pIB1; the construction of which is disclosed in Goeddel et al., 1979. Approximately 50 μg of plasmid pIB1 were digested with BamHI and EcoRI in substantial accordance with the teaching of Example 7A, and the desired ~0.453 kb insulin B chain structural gene-containing EcoRI-BamHI restriction fragment was isolated by polyacrylamide gel electrophoresis and electroelution. Approximately 0.5 μg of the desired fragment was obtained, suspended in 25 μl of TE buffer and stored at -20° C.

3. Isolation of the Proinsulin Structural Gene

The proinsulin structural gene was obtained from plasmid pHI7Δ4Δ1; the construction of plasmid pHI7Δ4Δ1 is disclosed in U.S. Pat. No. 4,530,904, as well as in the corresponding European Patent Office Publication #105608A1, published 4/18/84. Approximately 50 μg of plasmid pHI7Δ4Δ1 were digested with BamHI and EcoRI in substantial accordance with the teaching of Example 7A, and the desired ~0.705 kb proinsulin structural gene-containing EcoRI-BamHI restriction fragment was isolated by polyacrylamide gel electrophoresis and electroelution. Approximately 0.5 μg of the desired fragment was obtained, suspended in 25 μl of TE buffer and stored at -20° C.

B. Ligations

The following ligations were done in substantial accordance with the procedure of Example 5A. Six different ligations were performed in order to construct both trpLE1 and trpLE2 derivatives of each of the three structural genes isolated in Example 8A. Each ligation involved: 1 μl of the EcoRI- and BamHI-digested plasmid pBR322 DNA prepared in Example 7A; 4 μl of either the trpLE1- or trpLE2-encoding EcoRI restriction fragments prepared in Examples 2 and 4, respectively; and 4 μl of one of the EcoRI-BamHI structural gene-encoding restriction fragments isolated in Example 8A. Thus, plasmids pIALE1 and pIALE2 contain the trpLE1- and trpLE2-insulin A chain derivative genes, respectively; plasmids pIBLE1 and pIBLE2 contain the trpLE1- and trpLE2-insulin B chain derivative genes, respectively; and plasmids pPILE1 and pPILE2 contain the trpLE1- and trpLE2-proinsulin derivative genes, respectively.

C. Transformations

Each of the six ligations of Example 8B were individually used to transform *E. coli* RV308 in substantial accordance with the procedure of Example 5B2. The desired transformants were identified by their ampicillin-resistant, tetracycline-sensitive phenotype and by analysis of the transformant's plasmid DNA.

EXAMPLE 9

Preparation and Analysis of Cell Extracts

A. Cell Culture

Overnight cultures of *E. coli* K12 RV308/pIGF201, *E. coli* K12 RV308/pIGF202, *E. coli* K12 RV308/pIGF203, *E. coli* K12 MM294/pIGF201, *E. coli* K12 MM294/pIGF202 and *E. coli* K12 MM294/pIGF203 were prepared in TY media supplemented with 100 μg/ml each of tryptophan and ampicillin. Plasmid pIGF203 has the unimproved trpLE sequence in front of and in reading phase with the IGFII structural gene but is identical to plasmids pIGF201 and pIGF202 in all other respects. The overnight cultures were grown to an optical density at 550 nm of ~4.5 absorbance units. The overnight cultures were diluted with M9 media *(without added tryptophan); several dilutions of each overnight culture were made in order to observe protein synthesis occurring in the cells both in early log phase and in early stationary phase. In this manner, 12 distinct cultures were prepared. The cultures were then incubated at 37° C. for 4–8 hours.
*M9 media is, per liter of H2O: 10 g of Na2HPO4. 7H2O; 3 g of KH2PO4; 0.5 g of NaCl, and 1 g of NH4Cl. The media was supplemented with: 400 μl 1M MgSO4; 40 μl 1M CaCl2; 12.5 ml 20% casamino acids; 12.5 ml 40% glucose; and 10 mg/ml ampicillin.

B. Preparation of Cell-Extracts

The cultures were grown in the absence of tryptophan for varying lengths of time. Then, 1 ml of each culture was removed; the optical density at 550 nm was determined, and the cells were collected by centrifugation.

The cell pellet was resuspended in the amount of loading buffer (0.125M Tris-HCl, pH 6.8; 2% SDS; 3% glycerol; 0.005% bromphenol blue; and 6M Urea) necessary to form a suspension at 20 absorbance units per ml, as determined by the optical density measured before collecting the cells. The sample was boiled 5–10 minutes, and then 7 μl of each sample were loaded onto a SDS-polyacrylamide gel (SDS-PAGE) and electrophoresed with ~50 mA current until the bromphenol blue was near the bottom of the gel.

The gel was stained overnight in Fairbank's A stain: 0.5 g Coomassie brilliant blue; 250 ml isopropanol; 100 ml glacial acetic acid; and 650 ml H2O. The gel was then stained 3–4 hours in Fairbank's B stain: 0.05 g Coomassie brilliant blue; 100 ml isopropanol; 100 ml glacial acetic acid; and 800 ml H2O. The gel was destained in 10% acetic acid and then photographed.

The optical density readings at 550 nm, taken before cell harvest, are shown in Table II. The picture of the stained gel is presented in FIG. 8 of the accompanying drawings.

TABLE II

| E. coli culture | Lane # (FIG. 8) | O.D. 550 (absorbance) | Incubation Time (hours after dilution) |
|---|---|---|---|
| RV308/pIGF201 | 1 | 0.65 | 4.5 |
| RV308/pIGF202 | 2 | 0.48 | 4.5 |
| RV308/pIGF203 | 3 | 0.51 | 6.0 |
| RV308/pIGF201 | 4 | 2.9 | 8.0 |
| RV308/pIGF202 | 5 | 2.3 | 8.0 |
| RV308/pIGF203 | 6 | 0.80 | 8.0 |
| MM294/pIGF201 | 7 | 0.67 | 4.5 |
| MM294/pIGF202 | 8 | 0.46 | 4.5 |
| MM294/pIGF203 | 9 | 0.27 | 6.0 |
| MM294/pIGF201 | 10 | 2.4 | 8.0 |
| MM294/pIGF202 | 11 | 1.9 | 8.0 |
| MM294/pIGF203 | 12 | 0.6 | 8.0 |

Lane 13 (FIG. 8) contains Bio-Rad's (32nd and Griffin, Richmond, CA 94804) Low Molecular Weight Protein Standards.

Figure 8:
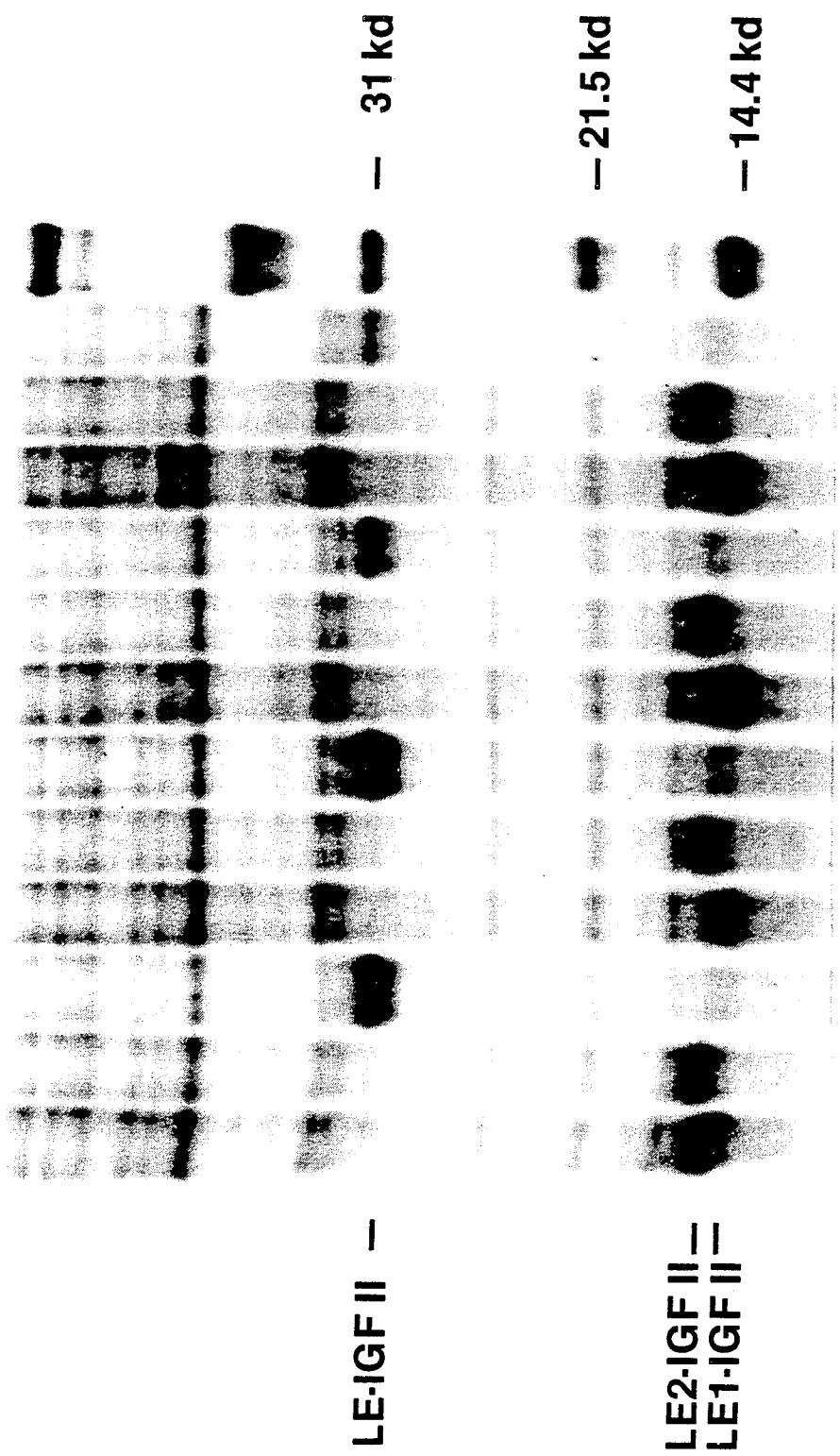
FIG. 8 is the result of polyacrylamide gel electrophoresis of cell protein containing the IGFII fusion product.

The data presented in Table II show that cells containing plasmid pIGF203 grew more slowly than cells containing either plasmid pIGF201 or plasmid pIGF202. Thus, the presence and expression of a shortened trpLE sequence has a lesser growth-retarding effect on *E. coli* K12 MM294 and *E. coli* K12 RV308 than does the presence and expression of the unimproved trpLE. FIG. 8, lanes 7–12, demonstrates that trpLE1 and trpLE2 drive greater production and accumulation of IGFII in *E. coli* K12 MM294 than does unimproved trpLE. Cell growth rate, product synthesis and product accumulation are all important factors in fermentation. The above evidence supports the claimed improved nature of the present invention by demonstrating that cells expressing trpLE1-IGFII or trpLE2-IGFII fusion polypeptides grow faster than cells expressing unimproved trpLE-IGFII fusion polypeptides. Additionally, the desired product represents a greater percentage of total cell protein when either trpLE1 or trpLE2, as compared to unimproved trpLE, is used in *E. coli* K12 MM294 to produce the fused gene product.

We claim:

1. In the derivative of the tryptophan operon promoter-operator-leader sequence wherein said sequence comprises a transcriptional activating sequence, a transitional activating sequence and a DNA coding region for a fused leader-trpE gene sequence from which the sequence encoding the carboxy terminus of the leader peptide, the attenuator region of the leader sequence and the proximal region of the trpE gene have been deleted, an improvement wherein the improvement comprises a shortened LE-encoding sequence, said shortened LE-encoding sequence being contained within a trpLE sequence comprising about 428 to about 548 deoxyribonucleotide pairs.

2. The shortened trpLE-encoding sequence of calim 1 which is about 428 deoxyribonucleotide pairs.

3. The sequence of claim 2 which is trpLE1.

4. The shortened trpLE-encoding sequence of claim 1 which is about 548 deoxyribonucleotide pairs.

5. The sequence of claim 4 which is trpLE2.

6. A recombinant DNA expression vector comprising:

(a) a tryptophan promoter-operator and shortened LE-encoding sequence of claim 1;
(b) a structural gene encoding a heterologous polypeptide, said gene positioned for expression from (a); and
(c) a replicon and selectable marker that provide for vector replication and allow for selection in a microorganism transformed by said vector.

7. The recombinant DNA expression vector of claim 6 wherein said structural gene is positioned for expression, and immediately adjacent, to a shortened trpLE-encoding sequence of about 428 to about 548 deoxyribonucleotide pairs.

8. The recombinant DNA expression vector of claim 7 which is a plasmid.

9. The recombinant DNA expression vector of claim 6 which is plasmid pLEBGH1.

10. The recombinant DNA expression vector of claim 6 which is plasmid pLEBGH2.

11. The plasmid of claim 6 which is pCZ20.

12. The plasmid of claim 8 which is pIGF201.

13. The plasmid of claim 8 which is pIGF202.

14. The plasmid of claim 8 which is pIALE1.

15. The plasmid of claim 8 which is pIALE2.

16. The plasmid of claim 8 which is pIBLE1.

17. The plasmid of claim 8 which is pIBLE2.

18. The plasmid of claim 8 which is pPILE1.

19. The plasmid of claim 8 which is pPILE2.

20. The recombinant DNA expression vector of claim 7 wherein the tryptophan promoter-operator and shortened trpLE sequence is trpLE1.

21. The recombinant DNA expression vector of claim 7 wherein the tryptophan promoter-operator and shortened trpLE sequence is trpLE2.

22. The recombinant DNA expression vector of claim 7 wherein the replicon and selectable marker allow for vector replication and selection in $E.$ $coli$.

23. The recombinant DNA expression vector of claim 22 wherein the selectable marker confers antibiotic resistance.

24. The recombinant DNA expression vector of claim 23 wherein the replicon and resistance-conferring selectable marker are selected from the group consisting of the replicons and resistance-conferring selectable markers from plasmids pBR322, pBR325, pBR324 and pKN402.

25. The recombinant DNA expression vector of claim 7 wherein the structural gene is selected from the group consisting of nucleotide sequences that code for insulin-like growth factor I, insulin-like growth factor II, bovine growth hormone, human growth hormone, human pre-growth hormone, porcine growth hormone, mammalian growth hormone, avian growth hormone, human insulin A chain, human insulin B chain, human proinsulin, human pre-proinsulin, interferon, urokinase, human tissue plasminogen activator, growth hormone releasing factor and interleukin II.

26. The insulin-like growth factor II structural gene of claim 25, wherein the coding strand of said structural gene has the nucleotide sequence:

| | | | |
|---|---|---|---|
| 5' G CTTATCGACC | GTCTGAAACT | CTGTGCGGCG | GCGAACTGGT |
| TGACACTCTG | CAGTTCGTTT | GCGGCGACCG | TGGCTTCTAC |
| TTCTCTCGTC | CGGCTTCTCG | TGTTTCTAGA | CGTTCTCGTG |
| GCATCGTTGA | AGAATGCTGC | TTCCGCTCTT | GCGACCTGGC |
| TCTGCTGGAA | ACTTACTGCG | CTACTCCTGC | TAAATCTGAA 3' | wherein
A is deoxyadenyl, G is deoxyguanyl, C is deoxycytidyl and T is thymidyl.

27. The recombinant DNA expression vector of claim 25 wherein the structural gene encoding insulin-like growth factor is contained on the ~230 bp EcoRI-BamHI restriction fragment of plasmid pCZ20.

28. A transformed gram-negative prokeryotic host cell comprising a recombinant DNA expression vector of claim 7.

29. The transformed host cell of claim 28 which is $Escherichia$ $coli$.

30. The transformed host cell of claim 28 which is $E.$ $coli$ RV308/pIGF201.

31. The transformed host cell of claim 28 which is $E.$ $coli$ RV308/pIGF202.

32. The transformed host cell of claim 28 which is $E.$ $coli$ RV308/pCZ20.

33. The transformed host cell of claim 28 which is $E.$ $coli$ RV308/pLEBGH1.

34. A transformed host cell which is $E.$ $coli$ R/R' wherein R is K12, K12 RV308, K12 HB101, K12 C600R$_k$—M$_k$—, K12 RR1, or K12 MM294 and wherein R' independently is a recombinant DNA expression vector of claim 7.

35. A transformed host cell which is $E.$ $coli$ R/R' wherein R is K12, K12 RV308, K12 HB101, K12 C600R$_k$—M$_k$—, K12 RR1, or K12 MM294 and wherein R' independently is a recombinant DNA expression vector of claim 6.

36. In the method for expressing a fused gene product in a microorganism transformed with a recombinant DNA vector which comprises a derivative of the tryptophan promoter-operator-leader sequence, said tryptophan sequence comprising a transcriptional activating sequence, a translational activating sequence, a fused leader-trpE sequence from which the sequence encoding the carboxy terminus of the leader sequence, the attenuator region of the leader sequence and the amino terminal region of the trpE gene have been deleted, and wherein said tryptophan sequence is fused in translational reading phase to a heterologous polypeptide-encoding sequence, an improvement wherein the improvement comprises transforming a microorganism with a recombinant DNA expression vector which comprises the shortened trpLE-encoding sequence of claim 1.

37. The method of claim 36 wherein the shortened trpLE-encoding sequence is about 428 deoxyribonucleotide pairs.

38. The method of claim 36 wherein the shortened trpLE-encoding sequence is about 548 deoxyribonucleotide pairs.

39. The method of claim 37 wherein the shortened trpLE-encoding sequence is trpLE1.

40. The method of claim 38 wherein the shortened trpLE-encoding sequence is trpLE2.

41. The method of claim 36 wherein said heterologous polypeptide-encoding sequence is positioned for expression, immediately adjacent, downstream and in translational reading phase with a shortened trpLE-encoding sequence of about 428 to about 548 deoxyribonucleotide pairs.

42. The method of claim 36 wherein said recombinant DNA vector is a plasmid.

43. The method of claim 41 wherein said recombinant DNA vector is a plasmid.

44. The method of claim 43 wherein the plasmid is selected from the group consisting of plasmids pIBLE1, pIBLE2, pCZ20, pIGF201, pIGF202, pIALE1, pIALE2, pPILE1 and pPILE2.

45. The method of claim 42 wherein the plasmid is selected from the group consisting of plasmids pLEBGH1 and pLEBGH2.

46. The method of claim 44 wherein the plasmid is pCZ20.

47. The method of claim 44 wherein the plasmid is pIGF201.

48. The method of claim 44 wherein the plasmid is pIGF202.

49. The insulin-like growth factor I structural gene of claim 27 wherein the coding strand of said structural gene has the nucleotide sequence:

| GCTTATCGAC | CGTCTGAAAC | TCTGTGCGGC | GGCGAACTGG |
|---|---|---|---|
| TTGACACTCT | GCAGTTCGTT | TGCGGCGACC | GTGGCTTCTA |
| CTTCTCTCGT | CCGGCTTCTC | GTGTTTCTAG | ACGTTCTCGT |
| GGCATCGTTG | AAGAATGCTG | CTTCCGCTCT | TGCGACCTGG |
| CTCTGCTGGA | AACTTACTGC | GCTACTCCTG | CTAAATCTGA A | wherein A deoxyadenyl, G. is deoxyguanyl, C is deoxycytidyl and T is thymidyl.

* * * * *

UNITED STATES PATENT AND TRADEMARK OFFICE
CERTIFICATE OF CORRECTION

PATENT NO. : 4,738,921
DATED : April 19, 1988
INVENTOR(S) : Belagaje, et al.

It is certified that error appears in the above-identified patent and that said Letters Patent is hereby corrected as shown below:

Claim 1, line 53 to 54, "transitional" should read -- translational --.
Claim 2, line 64, "calim" should read -- claim --.
Claim 27, line 17, "growth factor" should read -- growth factor I --.
Claim 49, lines 13 et seq., "GCTTATCGAC CGTCTGAAAC TCTGTGCGGC GGCGAACTGG
TTGACACTCT GCAGTTCGTT TGCGGCGACC GTGGCTTCTA
CTTCTCTCGT CCGGCTTCTC GTGTTTCTAG ACGTTCTCGT
GGCATCGTTG AAGAATGCTG CTTCCGCTCT TGCGACCTGG
CTCTGCTGGA AACTTACTGC GCTACTCCTG CTAAATCTGA A
         wherein A deoxyadenyl, G. is deoxyguanyl, C is
should read      deoxycytidyl and T is thymidyl."

-- 5'-GGCCCGGAAA CTCTGTGCGG CGCTGAACTG GTTGACGCTC
TGCAGTTCGT TTGCGGCGAC CGTGGCTTCT ACTTCAACAA
ACCGACTGGC TACGGCTCTT CTTCTCGTCG TGCTCCGCAG
ACTGGCATCG TCGACGAATG CTGCTTCCGT TCTTGCGACC
TGCGTCGTCT GGAAATGTAC TGCGCTCCGC TGAAACCTGC
TAAATCTGCT-3'
wherein A is deoxyadenyl, G. is deoxyguanyl, C is deoxycytidyl and T is thymidyl.

Signed and Sealed this

Twentieth Day of September, 1988

Attest:

DONALD J. QUIGG

Attesting Officer        Commissioner of Patents and Trademarks